US009776114B2

(12) United States Patent
Verdegan et al.

(10) Patent No.: US 9,776,114 B2
(45) Date of Patent: Oct. 3, 2017

(54) SYSTEM FOR MONITORING AND INDICATING FILTER LIFE

(71) Applicant: CUMMINS FILTRATION IP, INC., Columbus, IN (US)

(72) Inventors: Barry M. Verdegan, Stoughton, WI (US); Chad M. Thomas, Algood, TN (US); Peter K. Herman, Stoughton, WI (US)

(73) Assignee: Cummins Filtration IP, Inc., Columbus, IN (US)

( * ) Notice: Subject to any disclaimer, the term of this patent is extended or adjusted under 35 U.S.C. 154(b) by 0 days.

(21) Appl. No.: 14/718,345

(22) Filed: May 21, 2015

(65) Prior Publication Data

US 2015/0328568 A1 Nov. 19, 2015

Related U.S. Application Data

(63) Continuation of application No. 13/157,007, filed on Jun. 9, 2011, now Pat. No. 9,061,224.

(60) Provisional application No. 61/352,852, filed on Jun. 9, 2010.

(51) Int. Cl.
| | | |
|---|---|---|
| B01D 35/143 | (2006.01) | |
| B01D 27/10 | (2006.01) | |
| B01D 37/04 | (2006.01) | |
| G01M 3/02 | (2006.01) | |
| G01N 15/08 | (2006.01) | |
| F01N 11/00 | (2006.01) | |
| F02M 37/22 | (2006.01) | |
| F02D 41/22 | (2006.01) | |
| F02D 41/14 | (2006.01) | |

(52) U.S. Cl.
CPC ......... *B01D 35/143* (2013.01); *B01D 27/101* (2013.01); *B01D 37/046* (2013.01); *F01N 11/002* (2013.01); *F02M 37/22* (2013.01); *G01M 3/025* (2013.01); *G01N 15/0826* (2013.01); *F01N 2550/04* (2013.01); *F01N 2900/0402* (2013.01); *F01N 2900/0412* (2013.01); *F01N 2900/0416* (2013.01); *F02D 41/22* (2013.01); *F02D 2041/1433* (2013.01); *Y02T 10/47* (2013.01)

(58) Field of Classification Search
CPC ... B01D 35/143; B01D 27/101; B01D 37/046
USPC ........ 701/102, 101; 210/90, 87, 86, 85, 739, 210/741; 702/50, 182, 183
See application file for complete search history.

(56) References Cited

U.S. PATENT DOCUMENTS

| | | |
|---|---|---|
| 3,412,786 A | 11/1968 | Taylor |
| 4,107,037 A | 8/1978 | Cavanaugh et al. |
| 4,146,887 A | 3/1979 | Magnante |
| 4,154,586 A | 5/1979 | Jones et al. |
| 4,155,358 A | 5/1979 | Mcallister et al. |
| 4,231,768 A | 11/1980 | Seibert et al. |

(Continued)

OTHER PUBLICATIONS

International Search Report and Written Opinion, PCT/US2011/039812, Oct. 12, 2011.

(Continued)

*Primary Examiner* — Mahmoud Gimie
(74) *Attorney, Agent, or Firm* — Foley & Lardner LLP (57) ABSTRACT

Disclosed are systems, methods, and algorithms for monitoring and indicating filter life. In particular, the disclosed systems, methods, and algorithms may be utilized for monitoring and indicating the useful life of a filter in an internal combustion engine.

24 Claims, 11 Drawing Sheets

(56) References Cited

U.S. PATENT DOCUMENTS

| | | |
|---|---|---|
| 4,237,726 A | 12/1980 | Peterson et al. |
| 4,305,782 A | 12/1981 | Ostreicher et al. |
| 4,326,514 A | 4/1982 | Eian |
| 4,366,068 A | 12/1982 | Ostreicher et al. |
| 4,421,719 A | 12/1983 | Burleigh |
| 4,530,706 A | 7/1985 | Jones |
| 4,562,529 A | 12/1985 | Drummond |
| 4,684,380 A | 8/1987 | Leichnitz |
| 4,685,066 A | 8/1987 | Hafele et al. |
| 4,796,467 A | 1/1989 | Burt et al. |
| 4,859,340 A | 8/1989 | Hou et al. |
| 5,351,523 A | 10/1994 | Blackford et al. |
| 5,376,554 A | 12/1994 | Vo-Dinh |
| 5,512,882 A | 4/1996 | Stetter et al. |
| 5,659,296 A | 8/1997 | Debe et al. |
| 5,666,949 A | 9/1997 | Debe et al. |
| 5,685,895 A | 11/1997 | Hagiwara et al. |
| 5,796,007 A | 8/1998 | Panagotopulos et al. |
| 5,817,231 A | 10/1998 | Souza |
| 5,855,784 A | 1/1999 | Pike et al. |
| 5,856,198 A | 1/1999 | Joffe et al. |
| 5,968,371 A | 10/1999 | Verdegan et al. |
| 5,976,881 A | 11/1999 | Klingner |
| 6,009,404 A | 12/1999 | Eimer |
| 6,014,889 A | 1/2000 | Castor |
| 6,040,777 A | 3/2000 | Ammann et al. |
| 6,162,281 A | 12/2000 | Ammann et al. |
| 6,186,140 B1 | 2/2001 | Hoague |
| 6,375,725 B1 | 4/2002 | Bernard et al. |
| 6,497,756 B1 | 12/2002 | Curado et al. |
| 6,701,864 B2 | 3/2004 | Watson et al. |
| 6,736,980 B2 | 5/2004 | Moscaritolo |
| 6,812,035 B1 | 11/2004 | Spitler et al. |
| 7,174,273 B2 | 2/2007 | Goldberg |
| 7,442,237 B1 | 10/2008 | Gardner |
| 7,860,662 B2 | 12/2010 | Parham et al. |
| 7,922,914 B1 | 4/2011 | Verdegan et al. |
| 2003/0226809 A1 | 12/2003 | Zagone et al. |
| 2004/0217872 A1 | 11/2004 | Bhardwaj et al. |
| 2006/0259273 A1 | 11/2006 | Goldberg |
| 2008/0224838 A1 | 9/2008 | Rains et al. |
| 2011/0054811 A1 | 3/2011 | Contini et al. |

OTHER PUBLICATIONS

International Preliminary Report on Patentability, PCT/US2011/039812, Dec. 20, 2012.

SYSTEM FOR MONITORING AND INDICATING FILTER LIFE

CROSS-REFERENCE TO RELATED APPLICATIONS

The present application is a continuation of U.S. patent application Ser. No. 13/157,007, filed Jun. 9, 2011, which claims priority to U.S. Provisional Patent Application No. 61/352,852, filed Jun. 9, 2010. The contents of both applications are incorporated herein by reference in their entirety.

BACKGROUND

The field of the invention relates to filters. In particular, the field of the invention relates to systems for monitoring and indicating filter life for a filter in an internal combustion engine.

SUMMARY

Disclosed are systems for monitoring and indicating filter life. In particular, the disclosed systems may be utilized for monitoring and indicating the useful life of a filter in a machine such as an internal combustion engine.

The disclosed systems utilize methods for monitoring and indicating filter life. The disclosed methods may be utilized for determining and indicating useful life of a filter for filtering fluid in a given machine. Typically, the methods optimize cost-efficiency and value to a customer or purchaser of a filter by maximizing filter service intervals and full-life usage of a filter and minimizing available but unused filtration capacity of the filter prior to the end of filter-life. The methods may maintain fuel economy by reducing or limiting the total work required to pump fluid through the filter. The methods utilize an algorithm for calculating remaining useful filter life as disclosed herein. Initial constants for the algorithm are based on laboratory performance of the filter, historical performance of the filter, or both. Further, in the methods, the initial constants for the algorithm may be adjusted during filter usage based on actual performance of the filter, behavior or use of the machine in which the filter is utilized, or both. The algorithm may be utilized to calculate remaining useful filter life based on parameters that include, but are not limited to $\Delta P$, filter efficiency, and particle concentration downstream of the filter.

Suitable machines for the disclosed methods may include, but are not limited to, internal combustion engines and hydraulic machines. Suitable filters may include filters utilized for fuel-water separation, fuel filtration, lube filtration, coolants, hydraulics, and air.

Suitable machines for the disclosed methods may include an electronic control module (ECM) or a separate control module. In the methods, the initial constants for the utilized algorithm may be adjusted during operation based on behavior of the filter and resulting sensor input to the ECM which may be normalized or otherwise adjusted by the ECM, including historical behavior of the filter. In the methods, data may be obtained from the ECM and the obtained data may be used to calculate the volume of fluid flow through the filter. The volume of fluid flow thus calculated may be inputted into the algorithm utilized in the methods to indicate whether filter service is required. In some embodiments, the ECM may contain the algorithms and/or logic to do the analyses. In the disclosed methods, the initial constants for the algorithm typically may be adjusted during operation based on actual performance of the filter, behavior of the machine in which the filter is utilized, or both. The constants may be adjusted manually, automatically, or both. For example, in application, during operation, or in service, the initial constants for the algorithm typically may be adjusted during operation based on actual performance of the filter, behavior of the machine in which the filter is utilized, or both.

The initial constants may be adaptively varied or adjusted during operation, for example, if the observed pressure drop differs from the expected pressure drop based on the initial constants. For example, the initial constants may be adaptively varied or adjusted during operation based on parameters including, but not limited to, contaminant concentration, contaminant type, filter type, or a combination thereof.

In the disclosed methods, the initial constants may be adjusted during operation based on observed filter performance. Further, the algorithm utilized in the methods may be adaptively updated based on observed filter performance.

The disclosed methods may be utilized for determining and indicating useful life of a filter for filtering fluid in a given machine. In some embodiments, the methods provide an indication alert to a user that the filter is approaching an end-of-useful-life condition. For example, the methods may provide an indication alert to a user that the filter is approaching an end-of-useful-life condition based on total volume of fluid filter. Alternatively or in addition, the methods may provide an indication alert to a user that the filter is approaching an end-of-useful-life condition based on operating conditions to which the filter has been exposed.

In the methods the initial constants for the algorithm may be adjusted during operation during filter usage based on behavior or use of the machine in which the filter is utilized. For example, the initial constants may be adjusted during operation according to the number of start-up and shut-down events of the machine.

The algorithm in the methods may be adaptively adjusted for scheduling filter changes. In some embodiments, the algorithm is adaptively adjusted such that the filter is not replaced too soon, which may increase cost of operation for a machine that utilizes the filter. In other embodiments, the algorithm is adaptively adjusted such that the filter is not replaced too late, which may result in possible damage to the machine.

In the methods, the algorithm may be utilized as an adaptive tool which may be adjusted to more accurately estimate remaining useful life of said filter. The algorithm may be adjusted manually by service personnel. Alternatively or in addition, the algorithm may be adjusted automatically based on field experience to more accurately estimate remaining useful life of said filter.

The methods may include determining the volume of fluid filtered by the filter and using the algorithm to calculate remaining useful life of the filter based on the volume of fluid filtered. For example, the volume of fluid filtered may be calculated by tracking flow rate of fluid through the filter and by tracking time.

DETAILED DESCRIPTION

The present systems, methods, and algorithms may be described herein using several definitions, as set forth below and throughout the application.

Unless otherwise specified or indicated by context, the terms "a", "an", and "the" mean "one or more." For example, "a system" or "an algorithm" should be interpreted to mean "one or more systems" or "one or more algorithms."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus≤10% of the particular term and "substantially" and "significantly" will mean plus or minus>10% of the particular term.

As used herein, the terms "include" and "including" have the same meaning as the terms "comprise" and "comprising." For example, a "system including a sensor" should be interpreted to mean "a system comprising a sensor."

As used herein, the term "the" may be used interchangeably with the term "said." For example, "the system" may be interchangeably referred to as "said system."

As used herein, a "user" may include someone who is using a filter (i.e., a "customer" or an "operator"). A "user" further may include someone is monitoring the useful life of a filter to determine when the filter should be replaced (e.g., "service personnel").

The systems and methods disclosed herein may be utilize to monitor and indicate when the useful life of a filter is approaching its end based on the total volume of fluid that the filter has processed and/or the operating conditions to which the filter has been exposed. When the useful life of a filter is approaching its end, a user is alerted so that the filter may be replaced before the useful life of the filter has ended. The present systems and methods may provide advantages over systems and methods that utilize a change in pressure to determine when the useful life of a filter is approaching (i.e., "a ΔP-useful life indication"). In particular, the disclosed systems and methods may be utilized in fuel-water separators, fuel filtration, lube filtration, coolants, hydraulics, and air, in which filtration media effectiveness is a function of exposure to the total volume of fuel flowed through the filtration media regardless of particulate contaminant levels in the fuel, which is one parameter that can trigger a ΔP-useful life indication. In addition, under certain operating conditions, for instance significant number of start-up/shut-down events, the ability of filtration media to retain removed particles may be affected prior to a ΔP-useful life indication. In some embodiments, "a ΔP-useful life indication" may be reached when ΔP is greater than about 20, 21, 22, 23, 24, 25, 26, 27, 28, 29, or 30 kPa.

The disclosed systems and methods may be utilized to achieve a number of goals. In some embodiments, the disclosed systems and methods may be utilized to inform a user of the condition of a filter at an earlier point than indicated by other indicators, such as low power for a fuel filter or a ΔP indicator light. Also, by utilizing the disclosed systems and methods, a user may be alerted to when a filter should be replaced based on an approaching end to its useful life rather than based on time or mileage of usage for the filter. Further, the disclosed systems and methods permit users to maximize a filter product's useful life and minimize cost. In further embodiments, the disclosed systems and methods may be utilized to prevent and/or discourage the use of a filter product beyond the product's useful life, which may potentially compromise equipment utilizing the filter product in a harsh environment or in other applications. The disclosed systems and methods provide a user (e.g., an operator of a machine that incorporates the filter or service personnel that replace the filter) with an adaptive tool for scheduling filter changes, such that filter changes are not scheduled too soon thereby increasing cost of operation, and such that filter changes are not scheduled too late thereby resulting in damage to a machine that incorporates the filter (e.g., an engine). In further embodiments, the algorithm utilized in the disclosed systems and methods may be adjusted by users (e.g., service personnel that replace the filter) or automatically based on field experience to more accurately estimate remaining useful life of filter.

The disclosed systems and methods may include or utilize an electronic control module (ECM) and data captured by an ECM to calculate the volume of flow through a filter based on algorithms disclosed herein. For example, the disclosed systems and methods may use data captured by an ECM to calculate the volume of flow through a filter based on algorithm disclosed herein in order to indicate whether the filter is ending its useful life and should be replaced. The disclosed algorithms may be adjusted based on chosen factors (e.g., engine start-up/shut-down events) in order to better indicate when a filter is ending its useful life and should be replaced. The disclosed algorithms also may be utilized to indicate to a user that certain engine performance parameters should be adjusted, for example, engine performance parameters that typically alert a user that a filter should be replaced such as power limit.

The presently disclosed algorithms may be used to calculate remaining useful life of filter based on fluid volume filtered. Flow rate through the filter and time may be tracked and used to calculate volume filtered. The algorithm constants may be adjusted (e.g., manually or automatically) based on field experience, in order to improve accuracy over time with respect to estimating when a filter should be replaced. In this manner, the disclosed algorithm provides a tool that allows a user (e.g., an operator or service personnel)

to schedule filter service at more convenient times and, with use, improves accuracy of prediction with respect to end of useful life for the filter, thereby reducing costs and improving reliability. In manual operation, a user returns to a service center for appropriate algorithm adjustments, while in automatic operation, supporting sensors typically are present in the systems (e.g., on an engine) and are connected to a controller.

The disclosed algorithms may operate as follows. Initially, filter-life is defined in terms of miles or hours based on default values entered into the algorithm. These default values may be obtained based on lab testing or prior experience in order to estimate remaining filter or component life. In some embodiments, the algorithm constants may be adjusted automatically as the filter is used. For example, if the observed $\Delta P$ or duty cycle is not as expected, then algorithm constants can be modified accordingly. In other embodiments, the algorithm constants may be adjusted manually based on observed conditions. For example, if engine behavior is not as expected, or if upon change-out, a filter appears to have remaining useful life or appears to have exceeded useful life.

As the filter is used, flow through the filter and time may be measured, the volume filtered may be calculated, and the remaining useful life of the filter may be determined using the algorithms disclosed herein. The constant values utilized in the algorithms may be adjusted such that the system continuously refines constant values (e.g., manually or automatically, as previously discussed), such that the algorithm becomes more accurate over time and becomes tailored to specific machines or applications.

The algorithm assumes that removal efficiency for any given filter is a function of $\Delta P$ and generally is independent of other factors. In other words, a given $\Delta P$ corresponds to a certain removal efficiency and defines the relationship between cumulative contaminant loading, M, and $\Delta P$, pressure drop, as $$\Delta P = A + B \exp(CM)$$

where:
A=constant and is assumed to be equal to the initial $\Delta P$ when M=0.
B=constant that determines the point in time or mass loaded where the $\Delta P$ transitions into exponential increase. The larger B is, the sooner the curve goes exponential. B=f(concentration) and the higher the concentration, the larger B is.
C=constant and reflects how steeply $\Delta P$ climbs during exponential phase. The larger C is, the steeper the climb. With the y-axis plotted on log scale, "C" indicates the slope of the line after the transition point is passed, as determined by "B". C=f(concentration, type of contaminants) and the more important soft contaminants are and the higher the concentration of soft contaminants, the larger C is. When filter test data is used to determine constants, this term can correct for differences in contaminant concentration and type (hard vs. soft).

Figure 5:
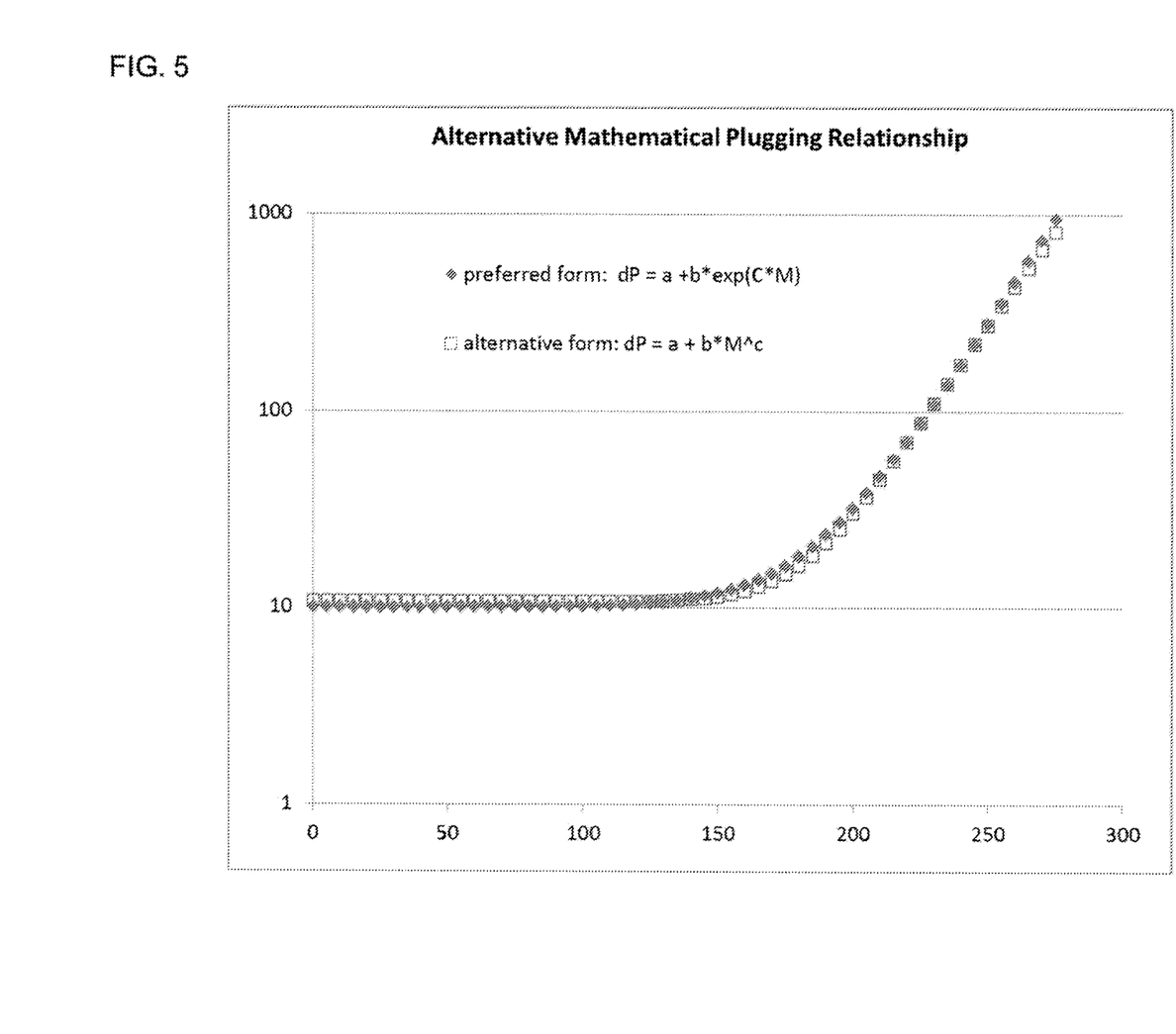
FIG. 5 illustrates plugging relationships based on equations $\Delta P = A + B*\exp(C*M)$ and $\Delta P = A + B*M^C$.
Figure 7:
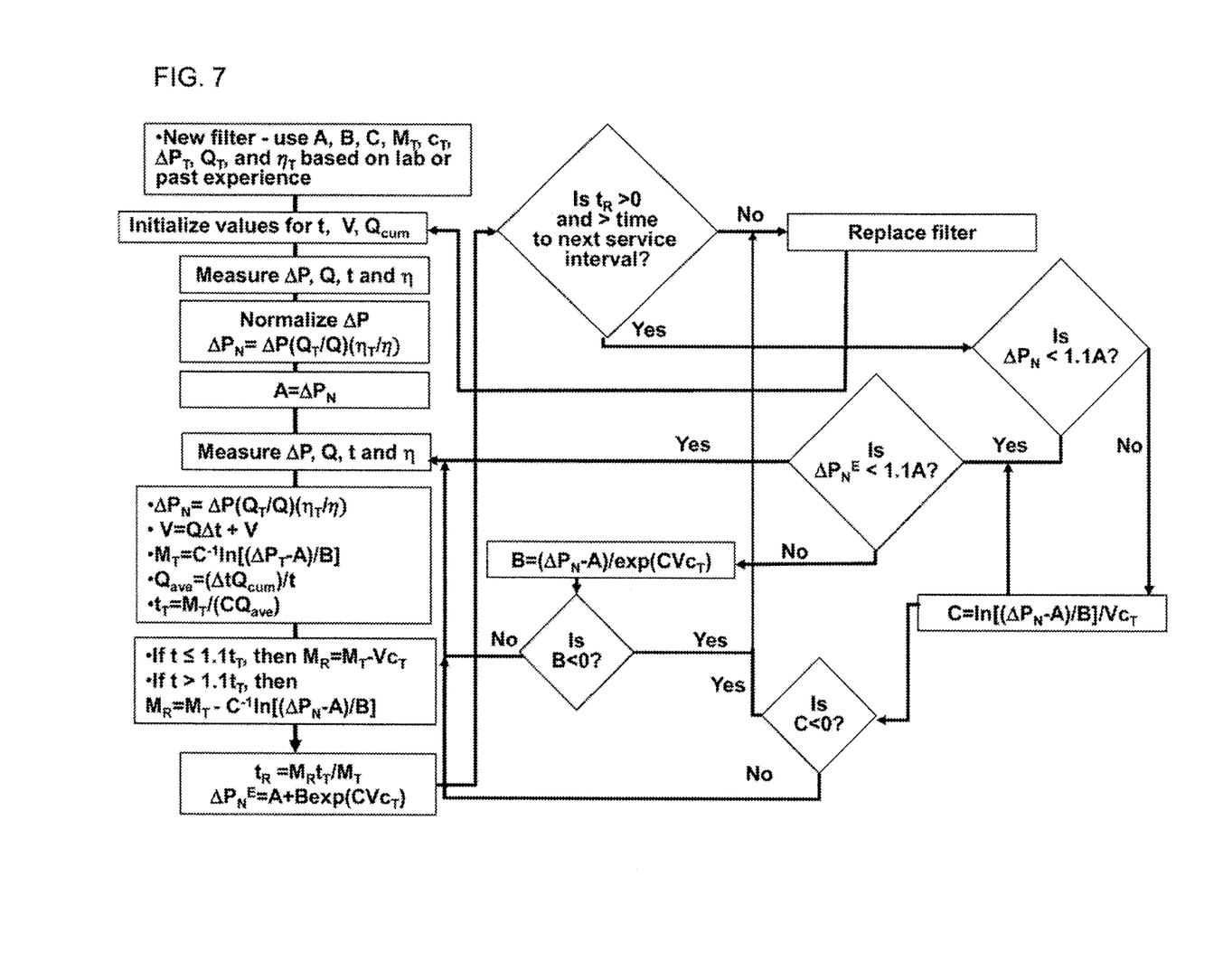
FIG. 7 illustrates a schematic diagram of one embodiment of an algorithm utilized in a system for monitoring and indicating filter life as contemplated herein including automatic correction steps.

FIG. 7 illustrates the use of this relationship as an algorithm in a system for monitoring and indicating filter life as contemplated herein including automatic correction steps. Other alternative equation forms can be identified that closely match the observed $\Delta P$ versus time response (or the mass-loaded or fluid filtered response). For example, $\Delta P = A + B*M^C$ generates very similar response (with very different values of B, and C vs. the exponential relationship (see FIG. 5)); or a modified form of this equation, such as $\Delta P = A + B*\exp(-M/C)$ which is functionally identical to the original form.

Figure 8:
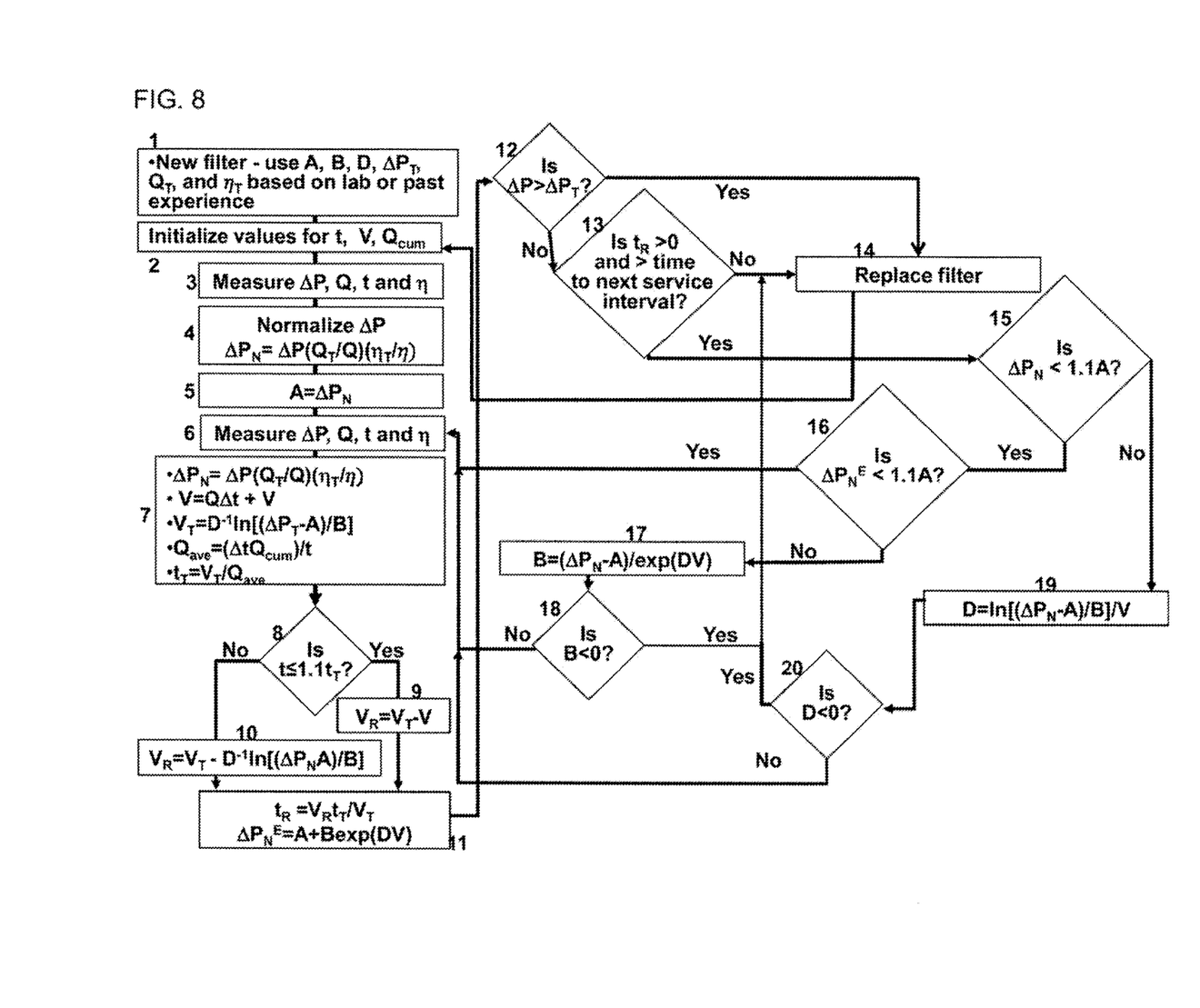
FIG. 8 illustrates a schematic diagram of one embodiment of an algorithm utilized in a system for monitoring and indicating filter life as contemplated herein including automatic correction steps which calculates the remaining fluid volume that can be filtered before its contaminant loading capacity is reached.

Alternatively, the pressure drop relationship can be expressed as a function of V, the volume of fluid filtered, as $$\Delta P = A + B \exp(DV)$$

$$D = C c_{ave}$$

where:
D=constant and reflects how steeply $\Delta P$ climbs during the exponential phase; and $C_{ave}$=average upstream contaminant concentration in the volume of fluid filtered. FIG. 8 illustrates the use of this relationship as an algorithm in a system for monitoring and indicating filter life as contemplated herein including automatic correction steps.

Because $\Delta P$ is a function of flow rate and fluid viscosity, it should be understood that, in order to use the previous equations the pressure drop data obtained for an operating system, pressure drop data may be normalized with respect to flow rate and viscosity. For convenience, it may be assumed in this description that the results may be normalized to the flow rate and viscosity conditions that were used under reference conditions, such as a laboratory, to generate the initial values for A, B, C and D. Moreover, it may be assumed that the $\Delta P$ varies proportionally in response to flow-rate and viscosity, as is typically found to be the case for viscous-dominated flow of liquids through filter devices where the filter element itself causes a majority of pressure drop. This assumption may be violated for poorly-designed filter housings containing "orifice-like" passages or constrictions that cause high inertial losses (dominating the total flow restriction), but those cases are not common. The normalized pressure drop, $\Delta P_N$, may be defined as $$\Delta P_N = \Delta P \frac{Q_T \eta_T}{Q \eta}$$

where:
$Q_T$=flow rate at reference condition
Q=flow rate
$\eta_T$=fluid viscosity at reference condition
$\eta$=fluid viscosity In FIGS. 7 and 8, this relationship is used to normalize pressure drop data in order to apply the appropriate algorithms to calculate remaining useful life. In cases where the $\Delta P$ does not vary proportionally in response to flow-rate and viscosity, other appropriate normalization relationship may be used.

Figure 2:
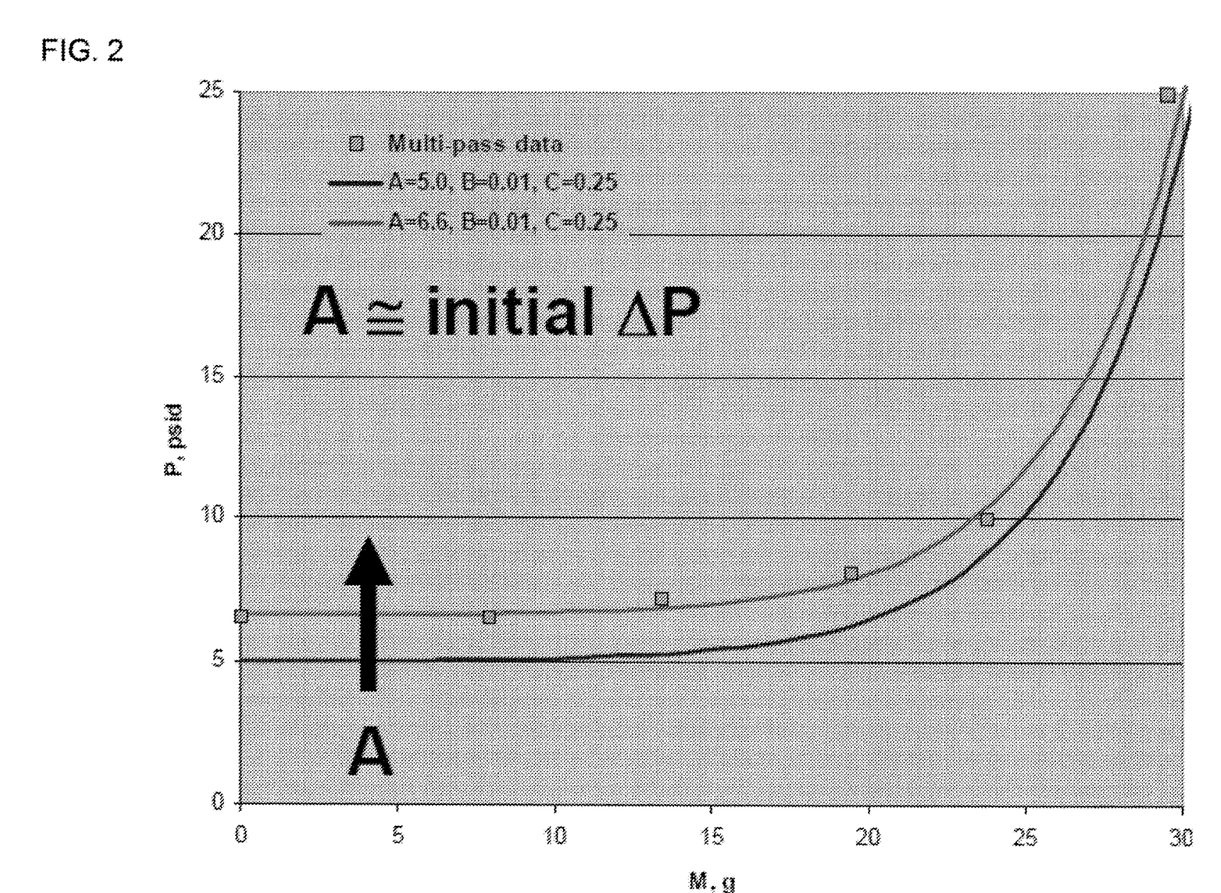
FIG. 2 provides a graphic illustration of the effect of variable "A" on the behavior of $\Delta P$.
Figure 3A:
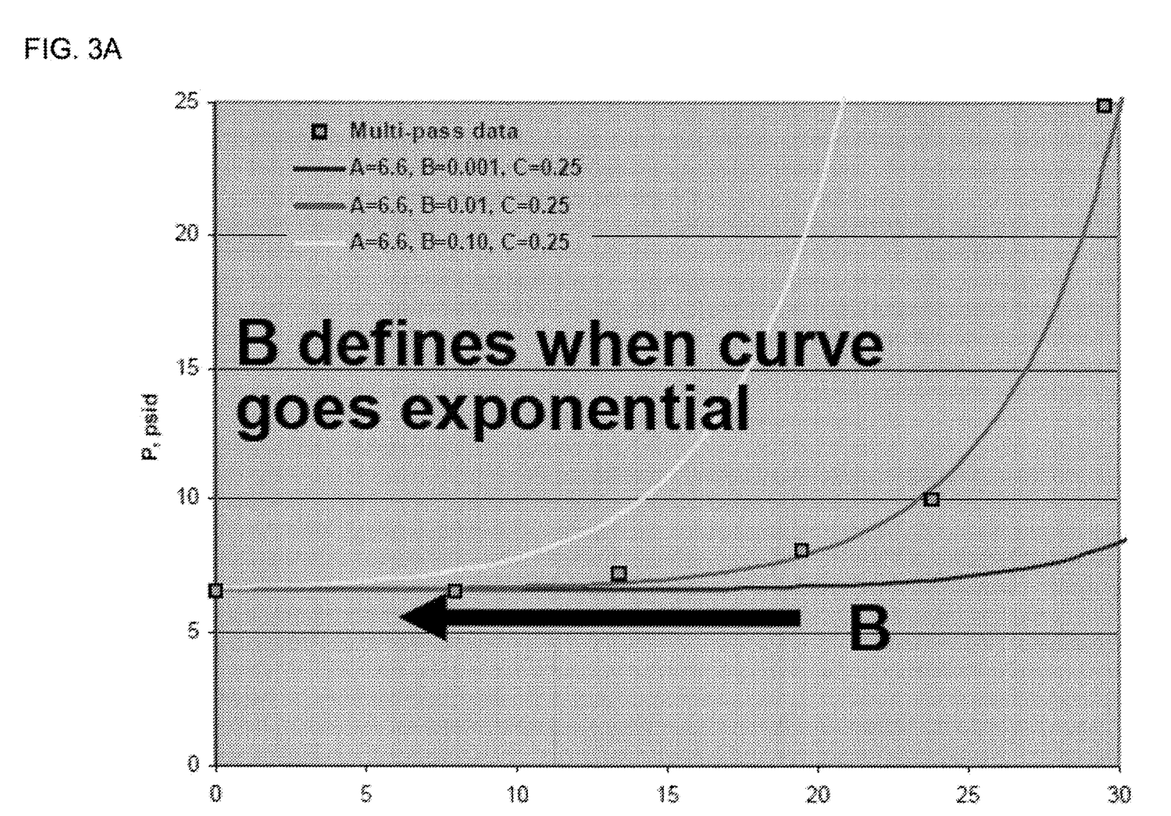
FIG. 3A is a linear plot that provides graphic illustrations of the effect of variable "B" on the behavior of ΔP.
Figure 3B:
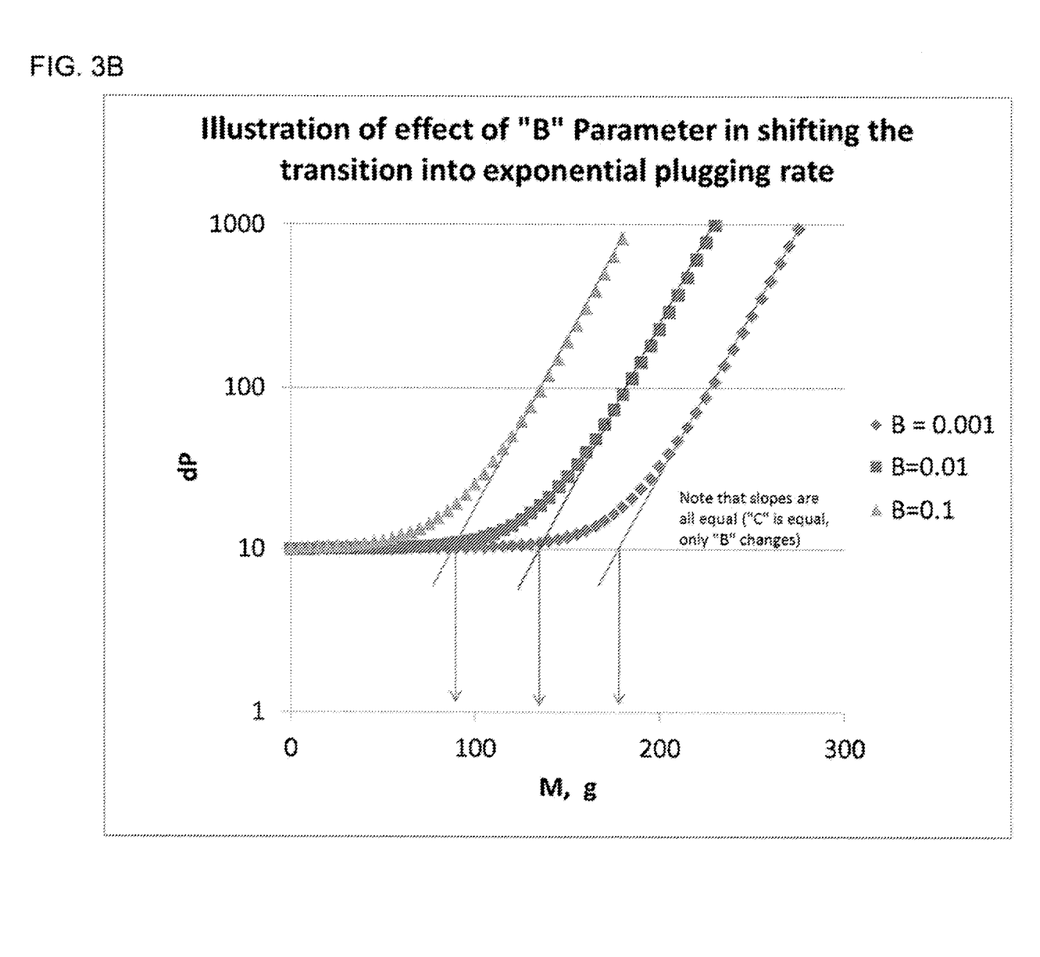
FIG. 3B is logarithmic plot that provides graphic illustrations of the effect of variable "B" on the behavior of ΔP.
Figure 4A:
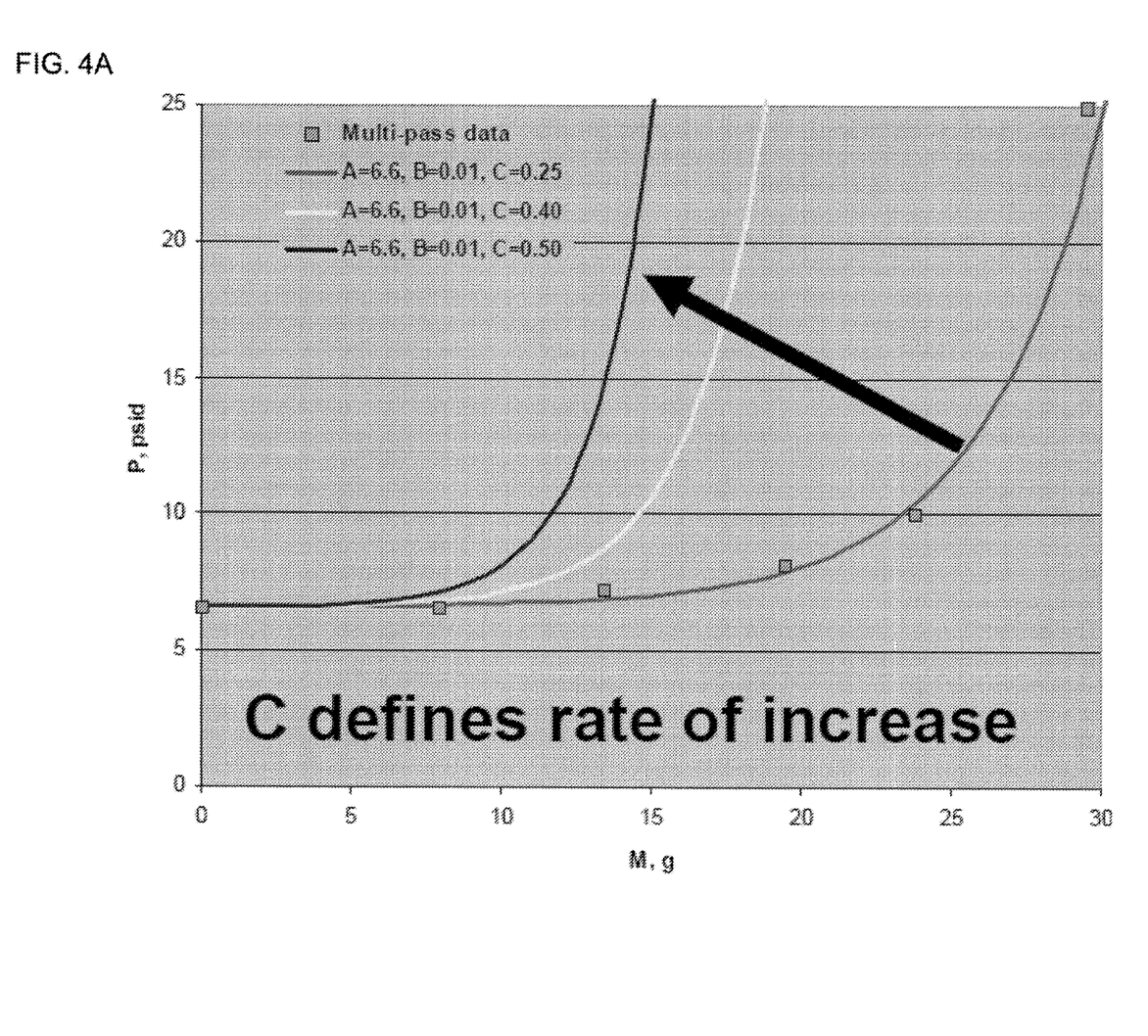
FIG. 4A is a linear plot that provides graphic illustrations of the effect of variable "C" on the behavior of ΔP.
Figure 4B:
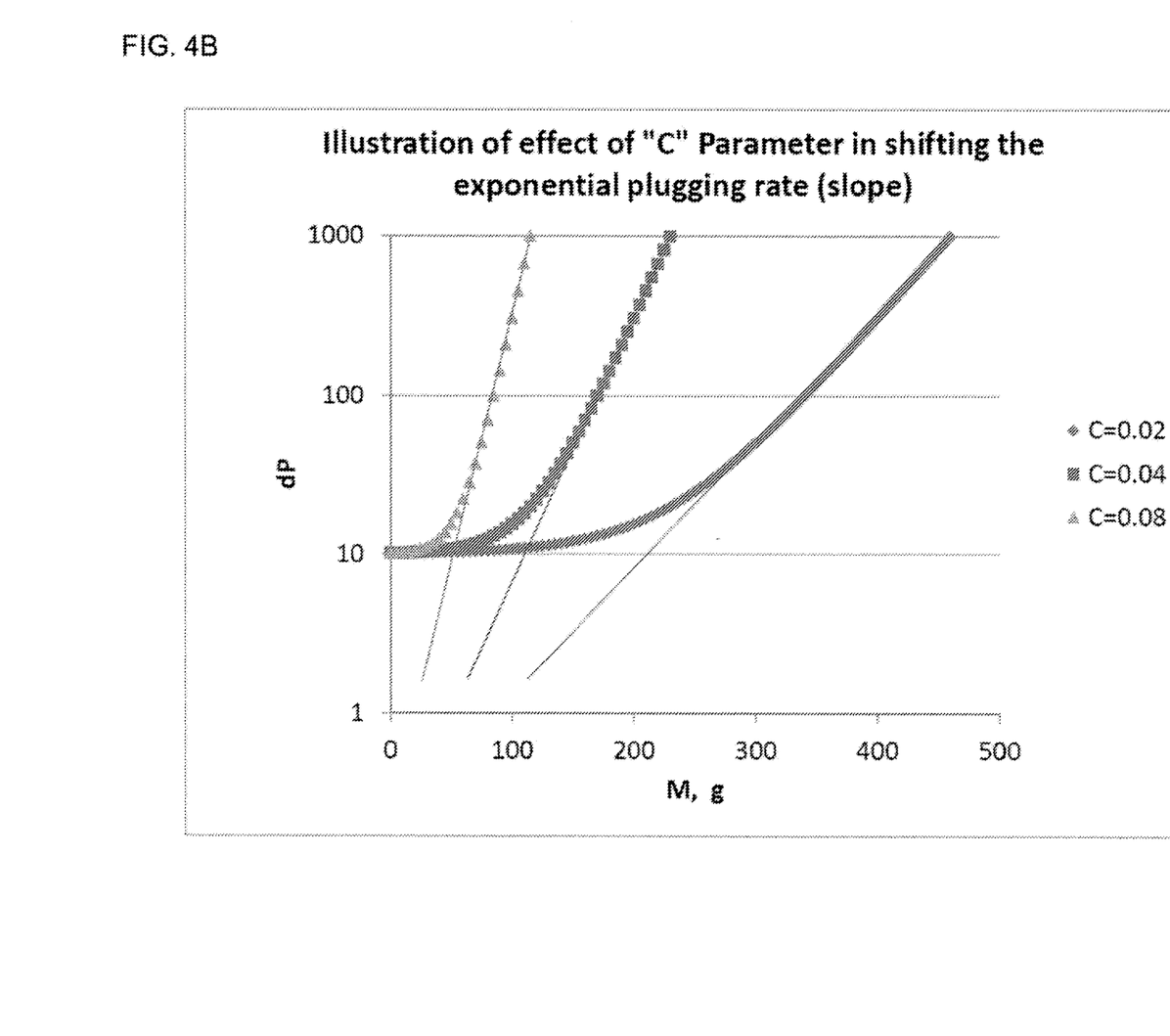
FIG. 4B is logarithmic plot that provides graphic illustrations of the effect of variable "C" on the behavior of ΔP.

FIGS. 2-4 show how $\Delta P$ changes as a function of M, in response to adjustments in A, B and C. M can be related to remaining useful life as follows:

$$M = \frac{1}{C} \ln\left(\frac{\Delta P \cdot A}{B}\right)$$

$$M_R = M_T - M$$

$$\frac{M_R}{M_T} = \frac{t_R}{t_T} = \frac{M_T - M}{M_T} = 1 - \frac{M}{M_T}$$

$$t_R = t_T\left(1 - \frac{M}{M_T}\right)$$

where:
M=cumulative contaminant loading
$M_R$=remaining contaminant holding capacity of filter
$M_T$=total contaminant loading capacity of filter
$Q_T$=flow rate used to determine capacity of filter $t_T$=time required for filter to be fully loaded at Q
$t_R$=estimated time remaining before filter is fully loaded with contaminant.

This can further be related to time, flow rate and volume filtered by:

$$M = Vc = \Sigma_0^t Qc\Delta t$$

where:
V=Volume filtered
t=Time
Q=Flow rate. Q=f(t) and depends on duty cycle.
c=Concentration. c=f(t) and depends on the operating environment, duty cycle, ingression, vibration, flow surges, and other application factors.

Figure 1:
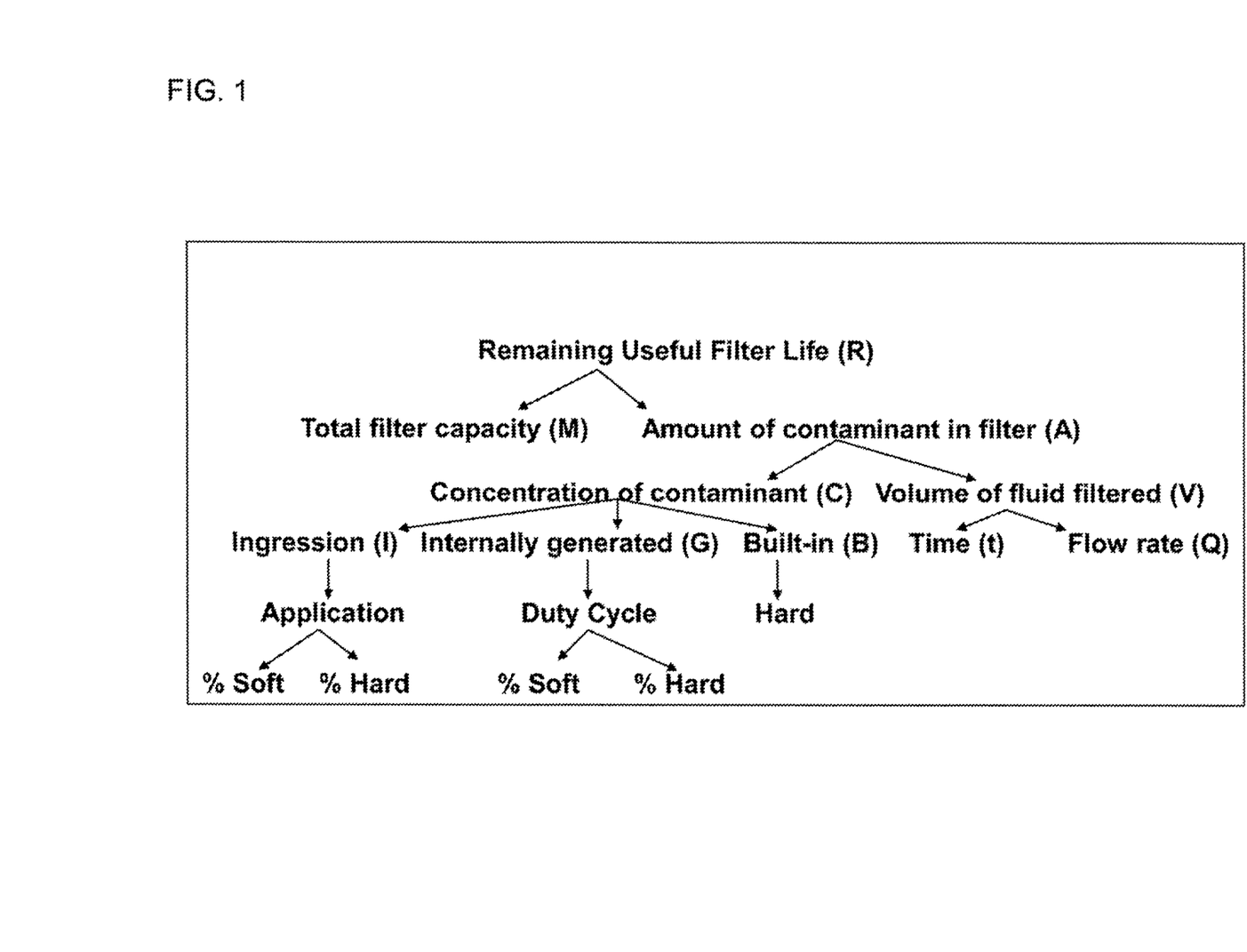
FIG. 1 illustrates a schematic diagram of contamination sources that provide bases for one embodiment of an algorithm utilized in the systems and methods for monitoring and indicating filter life as contemplated herein.

In order to calculate $t_R$, M must be known. M can be estimated using the equations presented above. M is directly proportional to V, assuming constant concentration. M can be estimated more accurately if Q and/or c as a function of time can be determined or is known. FIG. 1 provides a schematic diagram of contamination sources that may provide bases for the algorithm.

Alternatively, $t_r$ can be calculated from V as follows:

$$V = \frac{1}{D}\ln\left(\frac{\Delta P \cdot A}{B}\right)$$

$$V_R = V_T - V$$

$$\frac{V_R}{V_T} = \frac{t_R}{t_T} = \frac{V_T - V}{V_T} = 1 - \frac{V}{V_T}$$

$$t_R = t_T\left(1 - \frac{V}{V_T}\right)$$

where:
$V_R$ remaining volume of fluid that can be filtered before the filter reaches its contaminant holding capacity of filter
$V_T$=total volume of fluid that can be filtered by a new filter before its contaminant loading capacity is reached
$Q_T$ flow rate used to determine capacity of filter
$t_T$ time required for filter to be fully loaded at Q
$t_R$=estimated time remaining before filter is fully loaded with contaminant.

This can further be related to time, flow rate and volume filtered by:
where:

$$V = \Sigma_0^t Q\Delta t = Q_{cum} t$$

t=Time
Q=Flow rate. Q=f(t) and depends on duty cycle.
$Q_{cum}$=Sum of the flow rate values for each time increment sampled by the system during current filter service interval.

Various corrections to the disclosed algorithm may be made over time in order to better estimate the remaining useful life of a filter make the algorithm more accurate with respect to estimating useful life. For example, a volume correction to the estimated remaining useful life may be performed based on deviation from expected average flow rate. A concentration correction to the estimated remaining useful life may be performed based on ΔP or knowledge of application. In a first instance, the algorithm assumes that removal efficiency is a function of ΔP as previously noted. An engine sensitivity correction to the estimated remaining useful life may be performed based on duty cycle. Duty cycle is a term used to describe the severity of the engine's operating conditions and application. It can be defined quantitatively or qualitatively in various ways. For example, quantitatively, duty cycle can be defined as the ratio of the time-weighted average produced power to the engine rated power; the percentage of time that the engine operates at rated power (or some fraction of rated power); the ratio of the time-weighted average fuel consumption rate to the fuel consumption rate at rated power output; the ratio of the time-weighted average exhaust temperature to the rated exhaust temperature at standard temperature and pressure (STP) ambient conditions; the ratio of the time-weighted turbocharger boost pressure or temperature to the boost pressure or temperature at rated power output conditions; the ratio of some function of time and temperature of oil sump or coolant to the same function operating at rated power conditions; or some combinations of two or more of the previously listed definitions. Duty cycle can also be expressed in descriptive terms, e.g., severe, moderate, light, using the previously mentioned quantitative definitions, or others, such as fuel economy. Duty cycle affects the magnitude and/or frequency of flow transients, as well as temperature, which may be utilized to perform an empirical correction. Duty cycle affects the overall generation of contaminants, both soft and hard.

Figure 6:
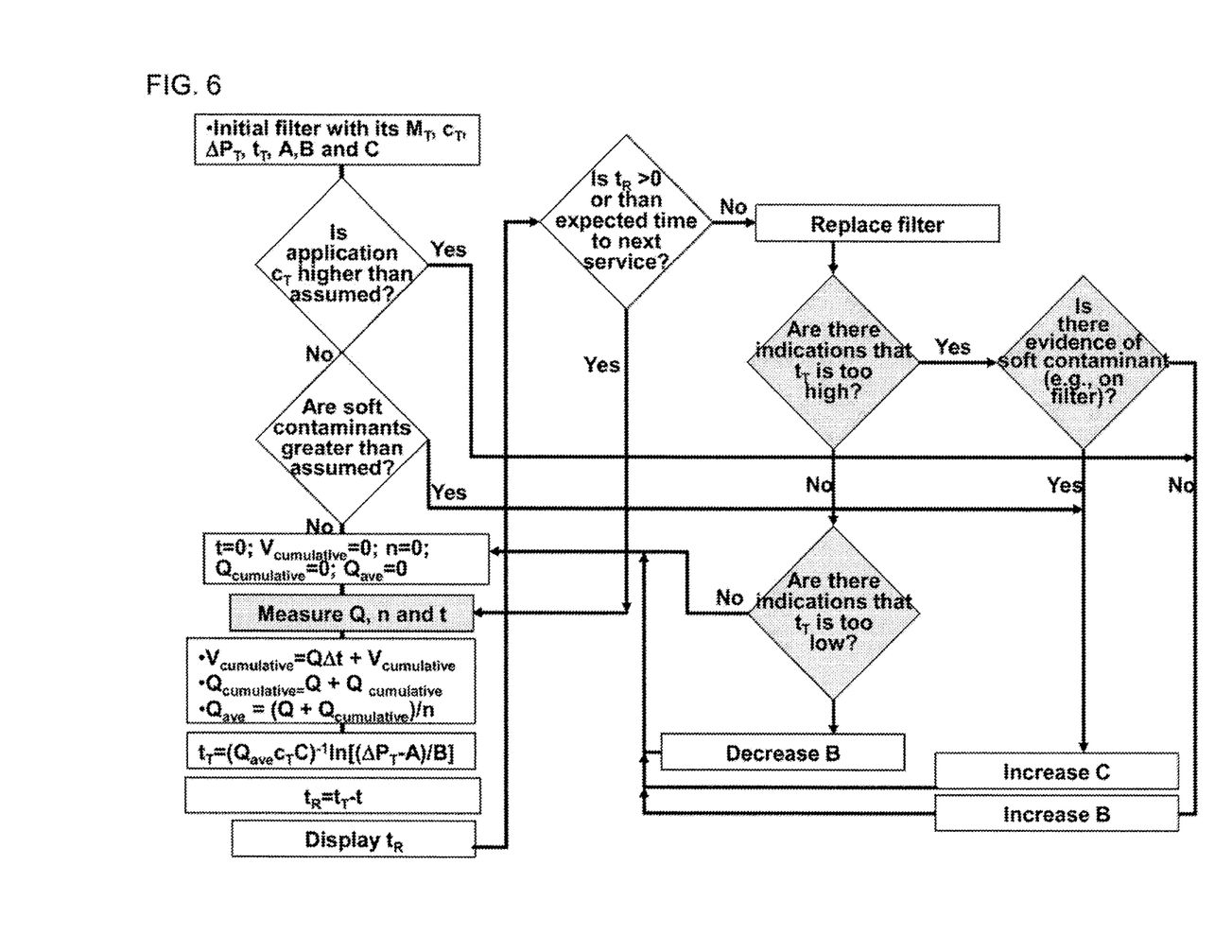
FIG. 6 illustrates a schematic diagram of one embodiment of an algorithm utilized in a system for monitoring and indicating filter life as contemplated herein including correction steps.

FIG. 6 shows an algorithm, in flow chart form, when the various constants of the algorithm are corrected manually, such as by service personnel. Examples of indications that $t_T$ is too low and that constants B and/or C needs to be manually readjusted, include, but are not limited to: high ΔP at change-out; loss of power (fuel); smoke (fuel); poor oil analysis; collapsed pleats; a slimy or coated filter; unscheduled repairs; fuel economy low or other indicator of harsher duty cycle; operating in dirty/dusty/off-road environment; and fluid supply/suppliers known to have poor quality.

Examples of indications that $t_T$ is too high and that constants B and/or C need to be manually readjusted, include, but are not limited to: ΔP low at change-out; Components in good shape at scheduled service interval; Very good oil analysis; Fuel economy high or other indicator of light duty cycle; Operating in clean environment; and Fluid supply/suppliers known to have high quality.

For the automatic version, illustrated in FIGS. 7 and 8 in flow chart form, adjustments in constant values may be performed automatically by the ECM or controller. Both service and automatic algorithms can be further simplified, if desired, by setting C or D as a true constant, A is a constant that is approximately equal to the initial ΔP when M=0;
M is cumulative contaminant loading;
B is a constant that determines the point where the ΔP transitions to an exponential rate of increase;

$$D = Cc_{ave};$$

C is a constant that reflects the exponential plugging slope; and
$c_{ave}$=average upstream contaminant concentration in the volume of fluid filtered and adjusting only B. In this case, B is a correction for both concentration and type of contaminant. This would simplify the calculation with minimal loss of accuracy and make adjustment easier, especially for manual application.

For the automatic version using filtered volume calculation, illustrated in FIG. 8 in flow chart form, adjustments in constant values may be performed automatically by the ECM or controller and the filter serviced as summarized. As shown in block 1, the first time when the system is used, initial values for A, B, D, $\Delta P_T$ (the terminal drop pressure), $Q_T$, $\eta_T$ based on reference conditions are entered into the system. The terminal pressure drop, $\Delta P_T$, is the pressure drop at which the filter should be replaced or serviced. In FIG. 8, blocks 2-5 indicate steps performed when a new filter is installed in which initial conditions for the new filter are entered and constant A is set based on the measured pressure drop, flow rate and viscosity. Blocks 6-10 and diamond 8 show measurement steps and calculation of the remaining volumetric capacity of the filter, $V_R$. Blocks 11-14 and diamonds 12-13 show the portions of the algorithm that determine whether or not the filter should be replaced or serviced. Diamonds 15-16 show the portions of the algorithm that determine whether or not the constants B and/or D need to be recalculated. Block 17 shows the portion of the algorithm in which the constant B is recalculated. Block 19 shows the portion of the algorithm in which the constant D is recalculated. Diamonds 18 and 20 show the portions of the algorithm that determine whether or not the filter is damaged and needs to be replaced. Other means of implementing the algorithms to optimize filter service intervals are anticipated, such as by storing historical values for A, B, C and/or D and comparing them to present values in order to determine whether or not the filter has been damaged or compromised or otherwise be replaced.

Figure 9A:
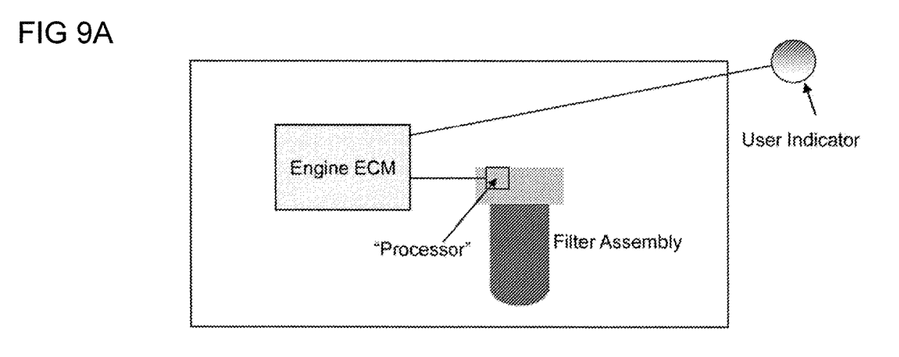
FIGS. 9A and 9B illustrate embodiments of a system for monitoring and indicating filter life as contemplated herein.
Figure 9B:
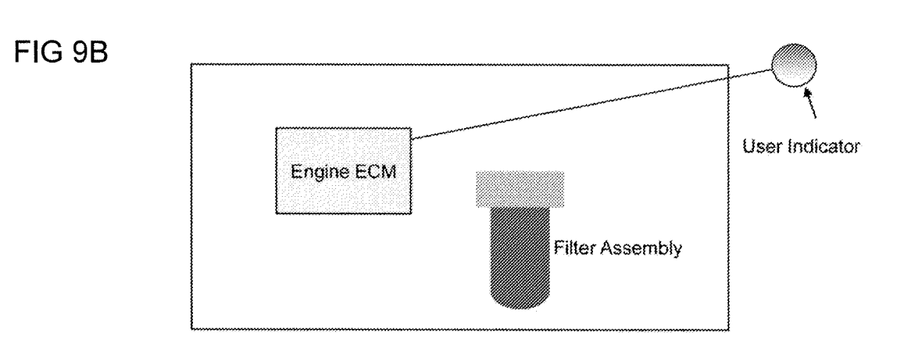

In some embodiments, the disclosed systems and methods may include or utilize hardware components as illustrated in FIGS. 9A and 9B. Specifically, the systems and methods may include or utilize one or more components selected from: a filter; a ΔP sensor to measure ΔP across the filter; a flow sensor to measure or estimate the flow rate through the filter; a timer to measure time at given flow rate or engine condition; a viscosity and/or temperature sensor to measure or estimate the viscosity of the fluid; a controller to accept sensor output, perform the calculations required by the algorithm, and output a signal indicative of the results of the algorithm calculation; an appropriate output device or means; and a sensor or other means to sense pressure flow rate, viscosity and/or temperature data which may be inputted into a device that utilizes the algorithm disclosed herein to correct pressure drop. Suitable sensors may include, but are not limited to, a flow meter, a separate ΔP sensor; a temperature sensor; a viscosity sensor; and a virtual sensor that makes the correction based on engine operating conditions.

In the foregoing description, certain terms have been used for brevity, clearness, and understanding. No unnecessary limitations are to be inferred therefrom beyond the requirement of the prior art because such terms are used for descriptive purposes and are intended to be broadly construed. The different configurations, systems, and method steps described herein may be used alone or in combination with other configurations, systems and method steps. It is to be expected that various equivalents, alternatives and modifications are possible within the scope of the appended claims. It is provisionally and preliminarily expected that the claims will include at least the following.

What is claimed is:

1. A system for determining and indicating a remaining useful life of a filter for filtering fluid in a machine having an internal combustion engine, the system comprising:
   the filter;
   a user indicator;
   a control module configured to:
      provide constants for a useful life calculation based on at least one of laboratory performance and historical performance, the useful life calculation calculating the remaining useful filter life of the filter based at least in part on a total volume of fluid filtered by the filter,
      utilize the useful life calculation for calculating the remaining useful filter life of the filter,
      adjust the constants of the useful life calculation during filter usage based on a behavior of the machine, wherein the behavior of the machine is a duty cycle of the internal combustion engine, and
      provide, via the user indicator, an indication alert to a user that the filter is approaching an end-of-useful-life condition based on the remaining useful filter life.

2. The system of claim 1, wherein the useful life calculation is utilized to calculate remaining useful filter life based on a pressure drop across the filter (ΔP).

3. The system of claim 1, wherein the useful life calculation is utilized to calculate remaining useful filter life based on filter efficiency.

4. The system of claim 1, wherein the useful life calculation is utilized to calculate remaining useful filter life based on particle concentration downstream of the filter.

5. The system of claim 1, wherein the machine is the internal combustion engine.

6. The system of claim 1, wherein the control module is an engine control module (ECM) of the internal combustion engine, and wherein the constants are adjusted during operation based on data obtained or processed by the ECM including historical behavior data.

7. The system of claim 6, wherein the ECM is further configured to:
   use ECM data to calculate the volume of fluid flow through the filter;
   use the useful life calculation to indicate remaining useful filter service life; and
   determine whether filter service is required.

8. The system of claim 1, wherein the machine is a hydraulic machine.

9. The system of claim 1, wherein the control module adjusts the constants during operation based on data obtained by a second control module that is separate from the machine including historical behavior data.

10. The system of claim 9, wherein the data is transmitted to a remote computer or controller that utilizes the useful life calculation.

11. The system of claim 1, wherein the control module is configured to receive a manual adjustment of the constants.

12. The system of claim 11, wherein the constants are adjusted manually during operation of the machine.

13. The system of claim 1, wherein the control module is configured to adaptively vary and adjust the constants during operation of the machine.

14. The system of claim 13, wherein the control module is configured to adjust the useful life calculation according to at least one of contaminant concentration, contaminant type, duty cycle, and filter type.

15. The system of claim 1, wherein the control module is configured to observe performance of the filter during operation, and to adjust the constants during operation based on observed filter performance.

16. The system of claim 1, wherein the control module is configured to observe performance of the filter during operation, and to adaptively update the useful life calculation either manually or automatically based on observed filter performance.

17. The system of claim 1, wherein the indication alert provided to the user is based at least in part on operating conditions to which the filter has been exposed.

18. The system of claim 1, wherein the filter is a fuel water separator.

19. The system of claim 1, wherein the control module is configured to adjust the constants during operation according to a number of start-up and shut-down events of the machine.

20. The system of claim 1, wherein the control module is configured to use the useful life calculation as an adaptive tool which can be adjusted by service personnel or automatically adjusted based on field experience to more accurately estimate remaining useful life of the filter.

21. The system of claim 1, wherein the control module is configured to determine the volume of fluid filtered by the filter, and to use the useful life calculation to calculate remaining useful life of the filter based on fluid volume filtered.

22. The system of claim 21, wherein the control module is configured to perform the determining step by calculating the volume of fluid filtered by the filter by tracking flow rate and time.

23. The system of claim 1, wherein the useful life calculation has a formula selected from:

$$\Delta P = A + B\exp(CM), \Delta P = A + B*M^C, \text{ and } \Delta P = A + B*\exp(-M/C)$$

wherein:
 $\Delta P$ is pressure drop across the filter;
 M is cumulative contaminant loading;
 A is a constant that is approximately equal to the initial $\Delta P$ when M=0;
 B is a constant that determines the point where the $\Delta P$ transitions to an exponential rate of increase; and
 C is a constant that reflects the exponential plugging slope.

24. The system of claim 1, wherein the useful life calculation has a formula:

$$\Delta P = A + B\exp(DV)$$

wherein:
 $\Delta P$ is pressure drop across the filter;
 A is a constant that is approximately equal to the initial $\Delta P$ when M=0;
 M is cumulative contaminant loading;
 B is a constant that determines the point where the $\Delta P$ transitions to an exponential rate of increase;
 $D = Cc_{ave}$;
 C is a constant that reflects the exponential plugging slope; and $c_{ave}$=average upstream contaminant concentration in the volume of fluid filtered.

* * * * *